US009308062B2

(12) United States Patent
Moriyama et al.

(10) Patent No.: US 9,308,062 B2
(45) Date of Patent: Apr. 12, 2016

(54) ARTIFICIAL TEETH, METHOD OF DETERMINING GRINDING PORTION, AND METHOD OF MANUFACTURING DENTURE

(71) Applicant: KABUSHIKI KAISHA SHOFU, Kyoto (JP)

(72) Inventors: Takeshi Moriyama, Kyoto (JP); Yusei Kadobayashi, Kyoto (JP)

(73) Assignee: KABUSHIKI KAISHA SHOFU, Kyoto (JP)

( * ) Notice: Subject to any disclaimer, the term of this patent is extended or adjusted under 35 U.S.C. 154(b) by 65 days.

(21) Appl. No.: 14/014,634

(22) Filed: Aug. 30, 2013

(65) Prior Publication Data

US 2013/0344460 A1 Dec. 26, 2013

Related U.S. Application Data

(62) Division of application No. 13/168,026, filed on Jun. 24, 2011.

(30) Foreign Application Priority Data

Jun. 25, 2010 (JP) ................................. 2010-145274

(51) Int. Cl.
*A61C 13/10* (2006.01)
*A61C 13/00* (2006.01)
*A61C 11/00* (2006.01)

(52) U.S. Cl.
CPC ......... *A61C 13/0024* (2013.01); *A61C 13/0004* (2013.01); *A61C 13/0006* (2013.01); *A61C 13/10* (2013.01); *A61C 11/00* (2013.01); *Y02P 20/52* (2015.11)

(58) Field of Classification Search
CPC .... A61C 13/00; A61C 13/10; A61C 13/0004; A61C 13/0024; A61C 13/0006; A61C 11/00; Y02P 20/52

See application file for complete search history.

(56) References Cited

U.S. PATENT DOCUMENTS 2,300,577 A 11/1942 La Due et al.
4,264,308 A 4/1981 Tanaka
(Continued)

FOREIGN PATENT DOCUMENTS

DE 198 38 238 3/2000
JP 5-95968 4/1993
(Continued)

OTHER PUBLICATIONS

USPTO Office Action (OA) issued Nov. 7, 2014 in related U.S. Appl. No. 13/168,234.
(Continued)

*Primary Examiner* — Ralph Lewis
(74) *Attorney, Agent, or Firm* — Wenderoth, Lind & Ponack, L.L.P.

(57) ABSTRACT

An artificial tooth where an occlusal surface is formed by grinding has a reference point that represents a position and an angle of the artificial tooth when an occlusal surface of the artificial tooth is obtained by an occlusal-surface form measuring apparatus. The reference point is a convexed spherical surface or a concaved spherical surface arranged on the occlusal-surface. The spherical surface has three or more reference points. The convexed spherical surface is fit to the concaved spherical surface when the maxillary artificial tooth and mandibular artificial tooth are occluded. The occluding portion of the artificial tooth has a grinding portion.

4 Claims, 10 Drawing Sheets

(56) References Cited

U.S. PATENT DOCUMENTS

| | | |
|---|---|---|
| 6,533,581 B1 | 3/2003 | Moenckmeyer |
| 7,160,110 B2 | 1/2007 | Imgrund et al. |
| 8,043,091 B2 * | 10/2011 | Schmitt .............. A61C 13/0004 433/196 |
| 8,364,301 B2 * | 1/2013 | Schmitt .................. A61C 1/084 700/118 |
| 8,423,166 B2 * | 4/2013 | Moriyama ......... A61C 13/0004 433/68 |
| 8,682,463 B2 * | 3/2014 | Moriyama ......... A61C 13/0004 433/68 |
| 9,173,724 B2 * | 11/2015 | Moriyama ......... A61C 13/0004 |
| 2005/0023710 A1 | 2/2005 | Brodkin et al. |
| 2005/0095562 A1 | 5/2005 | Sporbert et al. |
| 2005/0153255 A1 | 7/2005 | Sporbert et al. |
| 2006/0263749 A1 | 11/2006 | Koide |
| 2007/0190492 A1 | 8/2007 | Schmitt |
| 2008/0050700 A1 | 2/2008 | Weber et al. |
| 2008/0311537 A1 | 12/2008 | Minagi et al. |
| 2009/0042167 A1 | 2/2009 | Van Der Zel |
| 2009/0068617 A1 | 3/2009 | Lauren |
| 2009/0092946 A1 | 4/2009 | Yau et al. |
| 2009/0136902 A1 | 5/2009 | Zundorf et al. |
| 2009/0298017 A1 | 12/2009 | Boerjes et al. |
| 2011/0276159 A1 | 11/2011 | Chun et al. |

FOREIGN PATENT DOCUMENTS

| | | |
|---|---|---|
| JP | 8-287126 | 11/1996 |
| JP | 10-192305 | 7/1998 |
| JP | 10-225469 | 8/1998 |
| JP | 2000-316876 | 11/2000 |
| WO | 03/092536 | 11/2003 |

OTHER PUBLICATIONS

USPTO final Office Action issued Jul. 2, 2015 in related U.S. Appl. No. 13/168,234.

Partial European Search Report issued Aug. 21, 2012 in corresponding European Application No. 11 00 5210.

European Search Report issued Jan. 2, 2013 in corresponding European Application No. 11 00 5210.

Japanese Office Action (OA) issued Sep. 16, 2014 in corresponding Japanese Patent Application No. 2011-142012.

* cited by examiner

ARTIFICIAL TEETH, METHOD OF DETERMINING GRINDING PORTION, AND METHOD OF MANUFACTURING DENTURE

BACKGROUND OF THE INVENTION (1) Field of the Invention

The present invention relates to an artificial tooth having a reference point that facilitates grinding, a method for determining a grinding portion of artificial tooth, and a method for manufacturing a denture with artificial teeth.

(2) Description of Related Art

Heretofore, after making dentures, the dentures have been adjusted by rubbing the maxillary denture and the mandibular denture against each other in a process called grinding. The grinding has been performed as a process including two steps of: adjusting the dentures by attaching the dentures on an articulator and grinding little by little with a grinder while ascertaining contact portions between the maxillary denture and the mandibular denture; and then adjusting the dentures by applying a paste material containing abrasive particles to the occlusal surface and rubbing the maxillary denture and the mandibular denture against each other. Depending on the conditions of the dentures, the adjustment of the dentures has been performed using only one of these steps in some cases. However, there is no way to know whether portions to be ground are correctly determined. Thus, it has been difficult to determine whether the grinding is performed correctly.

Furthermore, it is necessary to perform grinding or an occlusal adjustment of the prepared prosthesis when the antagonist is a natural tooth. The occlusal adjustment of the prosthesis is adjusted by grinding the prosthesis little by little with a grinder to perform polish finishing while ascertaining contact portions of the prosthesis. However, there is also no way to know whether the portions to be occlusal adjusted was correctly determined, and it was also difficult to determine whether the occlusal adjustment was performed correctly.

Furthermore, dental students are educated about grinding and occlusal adjustment of prostheses at their universities. Although the teachers of each university carefully teach the grinding sites of prostheses and the occlusal adjustment thereof, much time has been required to improve the skills of the students because of difficulty in these areas. Students have a narrow window of opportunity to learn from one another a method of clearly recognizing a difference between the properly performed condition of grinding or occlusal adjustment, and the improperly performed condition in an objective manner. In addition, it is difficult for the students to know the degree to which they have acquired the skills. The students have to ask a dentistry instructor to confirm whether the grinding and occlusal adjustment steps are performed properly. There has been no way to know how to personally determine the grinding and occlusal adjustment in an objective manner.

JP-A-05-95968 discloses a dental model processing apparatus which is capable of drilling to insert a pin on a bottom surface of a dental model on an upper work table, and also capable of grinding inner and outer profile surfaces of the dental model on a lower work table. This processing apparatus is not intended for grinding an occlusal surface. Thus, it cannot be used for grinding the occlusal surface because of its structure.

JP-A-10-225469 discloses a method of arranging artificial teeth in which ground artificial tooth are used. However, a grinding adjustment is required because a small distortion or the like occurs in the production of a denture base. Thus, JP-A-10-225469 is not relevant to the present invention.

JP-A-2000-316876 discloses a drive apparatus for artificial-tooth grinding that intends to enhance an efficiency of grinding artificial tooth on an articulator. In the drive apparatus, a transducer linked to an oscillator circuit is installed as a driving unit for grinding on an articulator for grinding and occlusal adjustment of artificial tooth. However, the drive apparatus performs the grinding by rubbing the maxillary denture and the mandibular denture against each other.

Thus, it is difficult to perform arbitrary adjustment.

PRIOR ART DOCUMENT

JP-A-05-95968
JP-A-10-225469
JP-A-2000-316876

Conventionally, maxillomandibular grinding is a work operation performed by an experienced technician. In this grinding work, contact portions of the occlusal surface are determined and grinding thereof is performed little by little and repeated so as not to grind too much. However, it is the most difficult work to adjust a plurality of faces on the occlusal surface until the faces are rubbed. Although an experienced technician can reproduce the faces easily, less skilled persons have a lot of trouble with reproduction of the faces.

Completely adjusting the contact portions of the occlusal surface is difficult even for the experience technician and takes one hour or more.

An artificial tooth having portions where the upper and lower jaws come into contact with each other has an indeterminate form. Thus, the portions where the upper and lower jaws come into contact with each other are hardly ascertained. It has been difficult to clearly determine the contact position. An occlusal contact state is ascertained by sandwiching an articulating paper between the upper jaw and the lower jaw. A measurement error may occur due to the thickness of the articulating paper. Since only the contact portions of the articulating paper are stained, information about where the stained portion corresponds to the portion of the occlusal surface and about whether the contact is a dynamic contact or a static contact is not obtained.

In the occlusal adjustment, it has been necessary to select a method that does not damage a natural tooth by adjusting the artificial teeth along the profiles of the natural tooth.

The maxillomandibular grinding may be realized by grinding the artificial teeth little by little as the maxillomandibular contact state is confirmed by sandwiching the articulating paper between the upper jaw and the lower jaw. It is adjusted by increasing the contact faces between the upper jaw and the lower jaw. The contact portions of the articulating paper forms holes. Even if they are not in contact, when the upper jaw and the lower jaw are brought into close proximity with each other to a distance smaller than the thickness of the articulating paper, the articulating paper is compressed and thinned. The degree of thinness can be confirmed by optical penetration and the amount of gap can be confirmed by the transmission amount of light. As illustrated in FIG. 1, in order to bring each tooth in contact with the corresponding tooth, grinding is advanced with reference to the thickness of articulating paper while the contact portion between the upper jaw and the lower jaw is confirmed with the articulating paper.

Naturally, only the articulating paper can be relied upon under the conditions that the upper and lower jaws move freely on the articulator and it is hardly determined how far the contact areas thereof slide. Thus, an advanced technology has been required.

SUMMARY OF THE INVENTION

Therefore, an object of the present invention is to provide an artificial tooth having a reference point by which a grinding portion of a denture can be promptly determined without difficulty, and grinding can be easily performed. Another object is to provide a method for determining a grinding portion of an artificial tooth, a method for determining a grinding portion of an artificial tooth, and a method for preparing a denture using artificial teeth.

A first aspect of the present invention is an artificial tooth, where an occlusal surface is formed by grinding. The artificial tooth has a reference point that represents a position and an angle of the artificial tooth when the occlusal surface of the artificial tooth is obtained by an occlusal-surface form measuring apparatus.

The reference point is preferably a convexed spherical surface or a concaved spherical surface.

The number of the spherical surface is preferably 3 or more.

Preferably, the artificial tooth includes maxillary artificial tooth and mandibular artificial tooth, and the convexed spherical surface is fit to the concaved spherical surface when the maxillary artificial tooth and mandibular artificial tooth are occluded.

Preferably, the occluding portion of the artificial tooth has a grinding portion.

Preferably, the artificial tooth is a coupling tooth obtained by coupling at least two adjacent artificial teeth.

Preferably, the artificial tooth is a coupling tooth obtained by coupling four adjacent artificial teeth.

Preferably, the cerevix of each artificial tooth of the coupling tooth is formed of an artificial tooth form.

Preferably, the grinding portion exists in an occlusal surface.

A second aspect of the present invention is a method for determining a grinding portion of maxillomandibular artificial teeth in which the artificial teeth having a reference point of the first aspect are arranged. The method comprising:

a reference point data acquisition step of acquiring a three-dimensional reference point data of an artificial-tooth reference point of the artificial tooth having reference point and an articulator reference point representing a position of an articulator on which upper and lower jaws with the artificial teeth having reference point arranged are attached;

a reproduction step of reproducing the positions of artificial teeth of the upper and lower jaws attached on the articulator on a three-dimensional space from the acquired maxillomandibular three-dimensional reference point data; and a grinding data determination step of determining grinding data of a grinding portion under a dynamic condition or set condition from a portion surrounded by an image of upper and lower jaws on the three dimensional image in a reproduced occlusal state.

A third aspect of the present invention is a method for manufacturing a denture using artificial teeth having reference point according to the above first aspect, the method comprising:

an anterior-teeth arrangement step of attaching a patient's maxillomandibular model having a wax rim on an articulator through a spacer and arranging anterior teeth on the wax rim;

a preparation step for attachment of artificial teeth having a reference point of removing the spacer;

an attachment step for artificial teeth having a reference point of attaching the artificial teeth having the reference point on a molar portion of the wax rim on the maxillomandibular model; and a lost wax step of replacing the wax rim with an acrylic resin for denture plate by a lost wax process;

a grinding portion determination step of reading the artificial-tooth reference point and the articulator reference point and determining a grinding portion from a previously determined occlusal surface of the artificial tooth corresponding to the artificial-tooth reference point; and a grinding step of performing grinding of the grinding portion.

Preferably, an arrangement auxiliary tool is placed between the maxillomandibular front teeth in the preparation step for attachment of artificial teeth having reference point.

In this case, preferably, the arrangement auxiliary tool is provided with an arrangement auxiliary line.

According to a first aspect of the present invention, since the artificial teeth have reference points that represent a position and an angle of the artificial tooth, the positions of maxillomandibular artificial teeth can be reproduced in a three-dimensional space.

Since the reference point is in the form of a convexed spherical surface or a concaved spherical surface, the reference point can be easily calculated.

Since the convexed spherical surface can be fit to the concaved spherical surface when the maxillary artificial tooth and the mandibular artificial tooth are occluded, the arrangement of artificial teeth can be promptly performed in a simple manner.

Since the occluding portion of the artificial tooth has a grinding portion, the amount of grinding can be reduced.

Since the artificial tooth is a coupling tooth obtained by coupling at least two adjacent artificial teeth, the arrangement of artificial teeth can be promptly performed in a simple manner.

Since the cervix of each artificial tooth of the coupling tooth is formed of an artificial tooth form, the artificial teeth can be easily arranged on a wax rim.

Since the grinding portion exists in an occlusal surface, the amount of grinding can be further decreased.

According to the second aspect of the invention, from maxillomandibular three-dimensional reference point data, positions of artificial teeth of the upper and lower jaws attached to an articulator can be reproduced in a three-dimensional space. Thus, the grinding portion of a denture can be promptly determined in a simple manner.

In addition, since an exchange of data is ended in transfer and reception of the data of the reference point, the amount of the transmitted data amount can be reduced.

According to the third aspect of the present invention, a grinding portion is determined from a previously determined occlusal surface of the artificial tooth, which is performed corresponding to an artificial-tooth reference point. Thus, the grinding portion of a denture can be determined simply and quickly, and grinding can be performed on such a portion easily.

Since the arrangement auxiliary tool is used, the arrangement can be performed easily and the vertical relationship can be also determined easily.

DETAILED DESCRIPTION OF EMBODIMENTS

Figure 1:
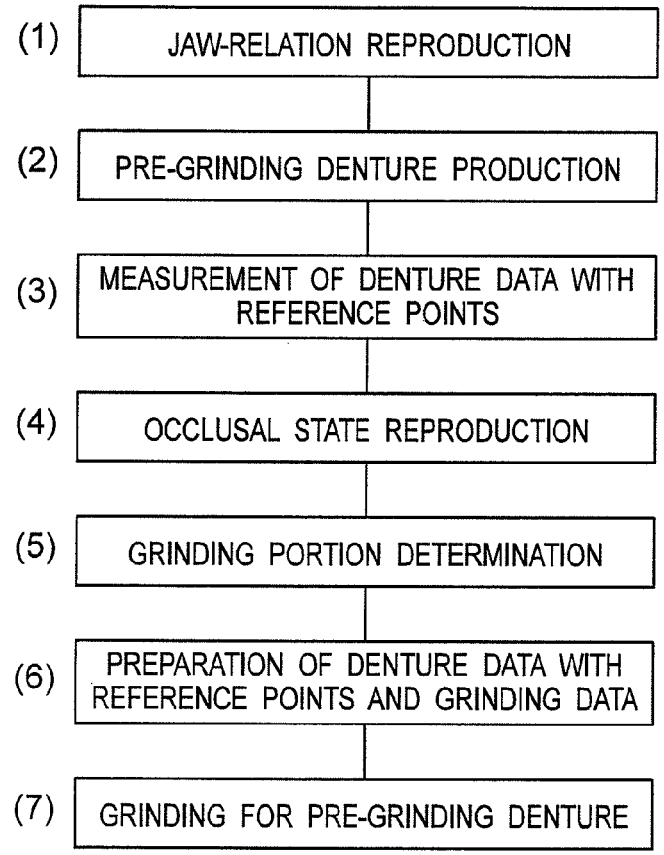
FIG. 1 is a flowchart illustrating a denture-grinding method according to the present invention.

The present invention include a method for performing grinding in denture production, a method for adjusting denture occlusion, and programs for executing these methods. The programs of the invention are employed for determining grinding portions of a denture, and grinding an undesired portion of an occlusal surface by using CAD/CAM.

A typical process for producing a denture is as follows:
1. An intraoral form of a patient is taken to prepare an impression.
2. An intraoral model of the patient is made of plaster using the impression and a constituent resin base plate is prepared on the model.
3. Wax is poured into a mold form and fixed in the shape of an arch. The wax is then mounted on the base plate to form a wax rim on which artificial tooth are arranged. A combination of this wax rim and the base plate is referred to as a bite plate.
4. The bite plate is applied to a patient to take a bite form of the patient.
5. Maxillary and mandibular models equipped with the bite plate is attached to an articulator to reproduce an occlusion state on the articulator.
6. Artificial tooth suitable for the patient are selected and maxillary anterior artificial teeth are arranged first on the maxillary wax rim and then mandibular anterior artificial teeth on the mandibular wax rim.
7. The maxillary height is slightly increased by adjusting an incisal pole of the articulator and mandible and maxillary molar artificial teeth are then arranged on the wax rim.
8. The incisal pole of the articulator is returned to the original state and an occlusal adjustment for grinding high portions is performed. In the occlusal adjustment, an articulating paper is sandwiched between the upper jaw and the lower jaw and a portion that strongly comes into contact with the opposite portion is ground.
9. A cervix (neck portion) state and a gingival regional state of the anterior teeth are reproduced.
10. The denture model with artificial teeth arranged on the bite plate is applied to the buccal cavity of the patient on a trial basis and information about required correction is then obtained.
11. Portions which should be corrected are corrected according to the information.
12. The denture model is separated in a flask (frame) and embedded in plaster and solidified.
13. The flask is heated to soften the wax of the denture model and the flask is removed to melt the wax, resulting in a mold.
14. A separation material is applied to the plaster portion of the mold, and resin for denture plate (synthetic resin)) is then poured into the mold. The upper and lower mold forms are combined together and then pressed by a press.
15. Excessive resin is removed and the upper and lower frames are set, followed by being subjected to heat to harden the resin.
16. The mold forms are removed and the plaster is then taken out to scrape out the denture.
17. The denture is attached to the articulator again and occlusal imbalance caused by contraction occurred in resin hardening is then corrected. Articulating paper is used in occlusal correction.
18. Occlusion when the jaw is moved back and forth and left and right is adjusted with an articulating paper (this adjustment is a last occlusal adjustment and called grinding).
19. Removing burrs from the resin, polishing is performed.

In the step of producing a denture, the intraoral form is taken, the wax rim is formed, the artificial teeth are arranged, and the wax is replaced with the resin by a lost-wax process. In this case, the contraction of the resin causes a positional displacement of artificial teeth and interference occurs when the artificial teeth are bitten as dentures by the upper and lower jaws. The grinding is the adjustment of such an interference portion. Even if the occlusion is correctly performed on the dentures, the grinding may be performed to change the occlusal relationship depending on the status of the buccal cavity of the patient. The adjustment is performed in corporation with the movement of the jaws of the patient. According to the present invention, a series of these operations is performed using a program.

Here, in the case of a denture-grinding method, full dentures are preferable. Alternatively, partial dentures may also be used even in the case where the upper and lower jaws are a combination of dentures.

1. Denture Grinding Method

The denture-grinding method of the present invention includes the following processes as illustrated in FIG. 1.
(1) Jaw-relation reproduction step
(2) Pre-grinding denture production step
(3) Measurement step for denture data with reference points
(4) Occlusal state reproduction step
(5) Grinding portion determination step
(6) Preparation step for denture data with reference points having grinding data
(7) Grinding step for pre-grinding dentures
(1) The jaw-relation reproduction step in which the jaw-relation reproduction conditions that can reproduce the conditions of the jaws of the patient are determined to reproduce the jaw relation will be described.

The jaw-relation reproduction step reproduces a positional relationship between the upper and lower jaws of the patient before the production of dentures. Usually, by using an articulator, the maxillomandibular movement is reproduced on the articulator by adjusting the movement of the condyle path of the articulator and incisal movement in corporation with the movement of the jaws.

It is necessary to decide moving directions that assume masticatory motion and opening/closing movement from the maxillomandibular centric occlusal position.

The conditions of the jaws of the patient include static conditions and dynamic conditions. Typically, the conditions include the position of the centric occlusal position and the directions of protrusive movement and lateral movement, and sometimes the direction of hinge movement.

These occlusal conditions can be reproduced by an occlusion-state reproducing apparatus, typically an articulator. The articulator can reproduce static relations and dynamic relations exactly.

The jaw-relation reproduction conditions include a sagittal condylar inclination, a balancing-side lateral condyle path, a regulatory mechanism of immediate side-shift, and a regulatory mechanism for an angle of lateral condyle path on the working side. Examples of the incisal path regulatory mechanism include a sagittal incisal path inclination and a lateral incisal path guide angle.

The method using the approximate values of the jaw movement in connection with the conditions of the patient is common. For example, the standard condylar distance is 110 mm, the distance between upper and lower arch is 110 mm, the maximum mandibular movement angle is 120 degrees, the inclination of sagittal condylar path is 30 degrees, and the angle of lateral condyle path is 15 degrees.

An important point is that it becomes clear how the upper jaw moves with respect to the lower jaw when the lower jaw is shifted from the centric occlusal position to the lateral movement.

As the simplest method, it is also possible to set the jaws so that the upper jaw slides forward at an angle of 10 degrees from the centric position in parallel to the lower jaw and the upper jaw further slides in the upper direction at an angle of 20 decrees with respect to the occlusal surface from the centric occlusal position.

In recent years, a method for directly reproducing a jaw movement has been investigated, and a jaw-movement measurement apparatus has been developed. The jaw movement may be directly acquired by a jaw-movement measurement apparatus so that the jaw movement may be reproduced by a jaw-movement reproducing apparatus.

(2) The pre-grinding denture production step of producing a pre-grinding denture will be described. Here, dentures are produced according to the jaw-relation reproduction conditions of the occlusion-state reproducing apparatus to produce pre-grinding dentures before the step of grinding.

The pre-grinding denture production step is a step of producing dentures according to the maxillomandibular relation obtained in the above occlusion-state reproduction step. In other words, the pre-grinding denture production step is a step of producing a normal denture (steps 6 and 7 in the above denture production process). In the typical process, a wax rim is formed, artificial teeth are arranged along the wax rim and a pre-grinding denture is prepared by a lost wax process. Here, the production method is not particularly limited but the pre-grinding denture can be produced by any typical procedure.

The pre-grinding denture is not ground, so that it cannot be correctly occluded on the occlusion-state reproducing apparatus yet. In order to carry out correct occlusion on the occlusion-state reproducing apparatus, the grinding of the occlusal surface is performed according to the present invention.

(3) The step for measuring denture data with reference points by a denture data measurement apparatus will be described. Here, the denture data measurement apparatus measures the denture data with reference points, comprising three-dimensional image data of the occlusal surface of the denture and reference points representing a positional relation between the occlusion-state reproducing apparatus and the denture.

In this step, the position of the pre-grinding denture in the occlusion-state reproducing apparatus is measured so that an occlusion state can be reproduced in a computer in addition to obtaining the 3D-data of the produced pre-grinding denture. By setting up the maxillomandibular relation of the occlusion-state reproducing apparatus in advance, the occlusion state can be reproduced.

At least three reference points are required for the respective upper and lower arches of the reproducing device (articulator). Alternatively, three sides may be used. One side and one point are preferable. Specifically, it may be configured of three needle-like form or spherical surface (preferably globular shape), or may be a combination of a straight side and spherical surface of the reproducing device. Here, the 3D-data is necessary to have reference points for correctly calculating the maxillomandibular relation to be reproduced on a computer. A spherical surface is preferable in order to match the 3D-data on a computer.

Figure 2:
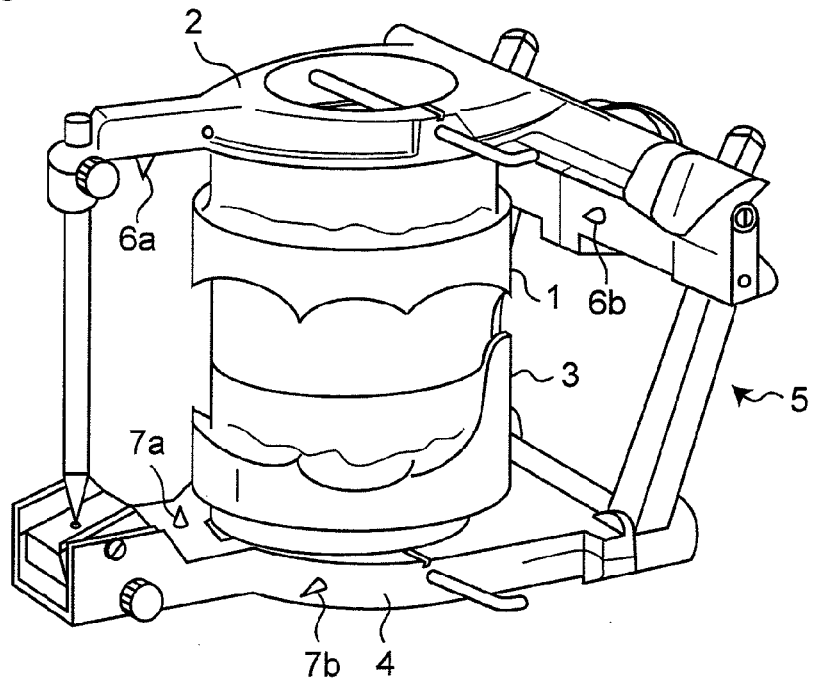
FIG. 2 is a perspective diagram illustrating a state where a maxillomandibular model is attached to an articulator having reference points.

The occlusion-state reproducing apparatus that determines the jaw-relation reproduction condition used for a denture grinding method is an articulator 5 having an upper arch 2 on which an upper jaw model 1 is attached and a lower arch 4 on which a lower jaw model 3 is attached. Preferably, as illustrated in FIG. 2, reference points 6a, 6b, and 6c and reference points 7a, 7b, and 7c are provided on the upper arch 2 and the lower arch 4, respectively.

(4) The occlusion-state reproduction step, which reproduces the occlusion state of the denture data with reference points by using the jaw-relation reproduction conditions, will now be described.

In this step, an occlusion state is reproduced on a computer. The maxillomandibular relation of the occlusion-state reproducing apparatus can be arbitrarily configured on the computer.

Here, the positional relationship between the upper and lower jaws can be correctly simulated in the space of the computer. In the computer, the static relationship between the upper jaw and the lower jaw is represented. This relationship includes the reference points which are used for acquiring 3D-data. In the space of the computer, the movements of upper and lower jaws are simulated so that the 3D-data of the upper and lower jaws represents a static relation.

Preferably, the mandibular orthogonal coordinate system of the lower jaw and the orthogonal coordinate system of the upper jaw are configured. To reproduce the maxillomandibular occlusal state, from an arbitrary positional relationship between the upper and lower jaws, a direction along which the orthogonal coordinate system of the upper jaw moves with respect to the orthogonal coordinate system of the lower jaw may be arbitrarily calculated.

Figure 3:
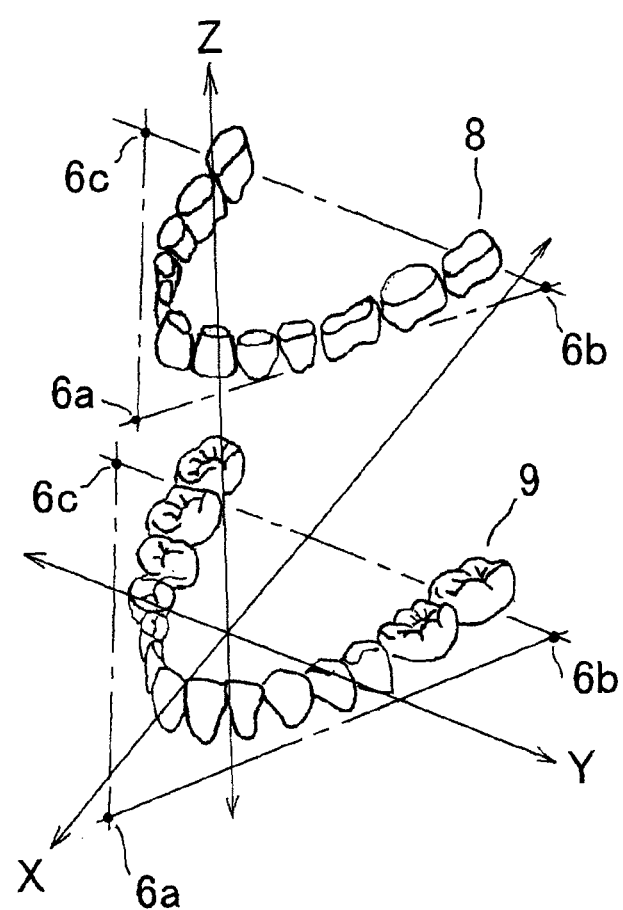
FIG. 3 is a diagram representing three-dimensional data of maxillomandibular occlusal surfaces on a three-dimensional space.

As illustrated in FIG. 3, the reference points on the orthogonal coordinate system of the lower jaw and the reference points on the orthogonal coordinate system of the upper jaw preferably coincide with the reference points on the computer to reproduce the relationship between the movement of the denture data 8 of the upper jaw and the denture data 9 of the lower jaw.

In each orthogonal coordinate system, the positions of reference points are defined and aligned with the denture data obtained in the step of measuring the denture data.

Figure 4:
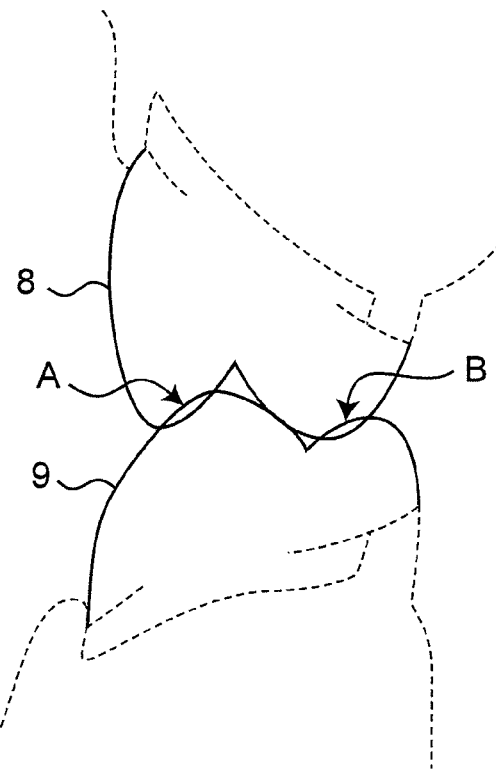
FIG. 4 is a diagram illustrating an occlusion state of the three-dimensional data of the axillomandibular occlusal surfaces.

As shown in FIG. 4, it can also set up so that an upper jaw orthogonal coordinate system may move to a lower jaw orthogonal coordinate system so that each coordinate axis performs the movement of the denture data 8 of the mandibular denture data 9 represented in the occlusion-state reproduction step.

(5) The determination step for the grinding portion, which determines grinding data under static conditions or defined conditions from a portion surrounded by the image of upper and lower jaws from the reproduced occlusion state, will be described.

Here, the region surrounded by the 3D data set in the step of reproducing the occlusion state (that is, as shown in FIG. 4, the region where the occlusion surface of the artificial tooth of the upper jaw and the occlusion surface of the artificial tooth of the lower jaw are overlapped) is observed.

In the case where the region surrounded by the 3D-data is small, the dentures lack in stability. Thus, an overlapped portion of maxillomandibular 3D-data is adjusted by the hinge movement of maxillary 3D-data or movement thereof in the direction of lowering an occlusal vertical dimension. If the overlapped portion of the 3D-data is large, there is no cusp of the tooth due to a large number of cuttings. Thus, an overlapped portion of maxillomandibular 3D-data is adjusted by the hinge movement of maxillary 3D-data or movement thereof in the direction of increasing the occlusal vertical dimension. The hinge movement or the shift in occlusal vertical dimension may be used in arbitrarily combination.

Figure 5A:
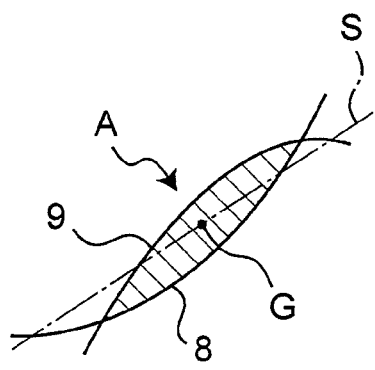
FIG. 5A is a diagram illustrating a portion surrounded by the three-dimensional data of the maxillomandibular occlusal surfaces.

Next, as illustrated in FIG. 5A, a grinding surface is determined by moving the maxillary 3D-data 8 or the mandibular 3D-data 9 so that the 3D-data overlapped portion A is frictionally moved during the movement of the upper and lower jaws. It is performed by cutting each 3D-data overlapped portion along the arbitrary defined grinding surface S at the time of forward movement, back movement, or lateral movement from the centric occlusal position.

Figure 5B:
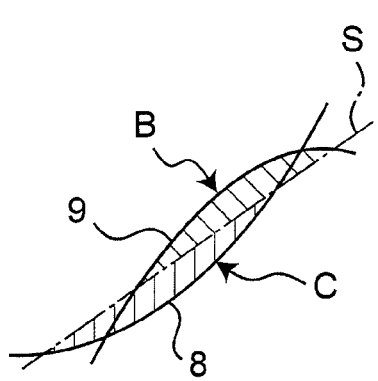
FIG. 5B is a diagram illustrating a grinding portion of the maxillomandibular occlusal surfaces.

Although the grinding surface S may not pass through the maxillomandibular 3D-data overlapped portion, preferably, it may pass through the overlapped portion between the maxillary 3D-data 8 and the mandibular 3D-data 9. As illustrated in FIG. 5B, cuspal portions B and C surrounded by the surface extended from the grinding surface S in the overlapped portion between 3D-data 8 and 9 are provided as cutting portions, respectively. These portions are referred to as grinding portions and the data thereof is referred to as grinding data.

The arbitrary defined grinding surface S is a surface extending in the direction of a forward movement, a backward movement, or a lateral movement and the angle of each surface is arbitrary defined with respect to an occlusal plane. It is preferable that the angle of the grinding surface S is set to 5 to 60 degrees with respect to the occlusal plane. An angle of a surface where the cusp of tooth touches is preferably 5 to 45 degrees in the forward or backward direction and 20 to 60 degrees in the lateral movement.

The movement direction is a direction along which the maxillary orthogonal coordinate system moves with respect to the mandibular orthogonal coordinate system at an arbitrary point within the range surrounded by the maxillary 3D-data and the mandibular 3D-data in the dynamic relation represented by the occlusion-state reproduction step. The movement direction is preferably linear. Alternatively, the movement direction may be curved. The movement direction may be approximate to a straight line. Alternatively, a curved line may be applied to the movement direction. In other words, the movement direction is a straight line or a curved surface. Preferably, it is a straight line or cylindrical surface.

Furthermore, the arbitrary point in range A surrounded by the maxillary 3D-data 8 and mandibular 3D-data 9 is the center of gravity G of the range surrounded by maxillary 3D-data 8 and the mandibular 3D-data 9.

When the range surrounded by the maxillary 3D-data 8 and the mandibular 3D-data 9 is represented by n points on the space, the center of gravity G is preferably calculated as X', Y', Z' obtained by converting X, Y, and Z axis of a mandibular orthogonal coordinate system and X, Y, and Z axis of a maxillary orthogonal coordinate system XYZ axis into those of the same orthogonal coordinate system, respectively, and dividing the sums of the values of the respective axes X, Y, and Z are divided by n. The grinding surface S is a plane including the movement direction of the upper jaw with respect to the lower jaw that passes through the values of X', Y', and Z'.

This movement direction is calculated by the reproduction method represented in the occlusion-state reproduction step. When the movement direction is reproduced by the articulator, these adjustment mechanisms can be reproduced on the computer in the case of an arcon type articulator or a condylar type articulator. The arcon type articulator is preferable.

The condylar distance of the articulator is 50 to 170 mm, preferably 80 to 140 mm, more preferably 100 to 120 mm. It is preferred to have an average condylar distance as a fixed value of 110 mm. A distance between the upper arch and the lower arch is about 80 to 120 mm. Any distance between the upper arch and the lower arch is allowable as long as it is determined where appropriate.

The condylar distance and the distance between the upper arch and the lower arch are calculated from numerical values previously defined by the condyle path regulatory mechanism and the incisal patch regulatory mechanism, which specify the maxillomandibular movement of the articulator.

Specifically, examples of the condyle path regulatory mechanism include an inclination of sagittal condylar path, a balancing-side lateral condyle path, a regulatory mechanism for immediate side-shift, and a regulatory mechanism for an angle of lateral condyle path on the working side. Examples of the incisal path regulatory mechanism include a sagittal incisal path inclination and a lateral incisal path guide angle.

An inclination of sagittal condylar path is −30 degrees to +90 degrees, preferably −0 degree to +50 degrees, more preferably −20 degrees to +80 degrees.

A balancing-side lateral condyle path is 0 degrees to +40 degrees, preferably +10 degrees to +20 degrees, more preferably 0 degree to +30 degrees.

A regulatory mechanism for immediate side-shift is 0 to 5 mm, preferably 0 to 8 mm, more preferably 0 to 10 mm.

A regulatory mechanism for an angle of lateral condyle path on the working side is −50 degrees to +60 degrees, preferably −40 degrees to +50 degrees, more preferably −30 degrees to +30 degrees.

A sagittal incisal path inclination is −30 degrees to +90 degrees, preferably-20 degrees to +80 degrees, more preferably −10 degrees to +75 degrees.

A lateral incisal path guide angle is −0 degree to +90 degrees, preferably −0 degrees to +50 degrees.

The maxillary orthogonal coordinate system is calculated with respect to the mandibular orthogonal coordinate system, which can move in accordance with these regulation mechanisms.

From the names or the like of commercial articulators, settings which can appropriately select only adjustment items are preferable. In the case where an unadjustable articulator is used, it is preferable that the fixed values of the articulator are fixedly entered without change when the name of this articulator is selected. The defined conditions are conditions being set to remove protruded portions to prevent upper and lower jaws from being caught while allowing them smoothly rubbing with each other.

The grinding data obtained in the present step is used as CAD data for grinding dentures. An NC program for processing in the grinding step for pre-grinding dentures is prepared. A computer numerical control (CNC), which controls a moving distance, a moving speed, and so on of tools in machine work by a computer, is used for grinding dentures. This process is referred to as CAM.

Figure 6:
FIG. 6 is a diagram illustrating a grinding portion of the occlusal surface.

FIG. 6 is a diagram illustrating faces to be ground in occlusal surfaces. Grinding is performed substantially in a bilaterally-symmetric manner. Thus, lead lines 1, 2, and 3 represent only one of jaws, respectively. When the upper and lower jaws are occluded, occlusal facets, where the upper and lower jaws make contact with each other, come into surface contact with the corresponding ones. Thus, the occlusal facets become surfaces being rubbed in accordance with the movement of the jaws.

Lead line 1 denotes posterior occlusal facets, lead line 2 denotes protrusive occlusal facets, and lead line 3 denotes balancing occlusal facets.

In other words, in the figure, reference numeral 1 denotes each of the surface portions to be ground at a certain angle, 2 denotes each of the surface portions to be ground at another angle, and 3 denotes the surface portions to be ground at a still another angle. However, these surfaces represented by these reference numerals are illustrative only. When considering occlusal static or dynamic relation, it is preferable to adjust or calculate the angles of the respective surfaces so that the surfaces are rubbed with the corresponding surfaces in their correct directions. Alternatively, however, these surface portions may be those to be ground almost at the same angle.

(6) The preparation step for denture data with reference points having grinding data, in which the denture data with reference points having grinding data, where denture data with reference points is additionally provided with grinding data, is prepared, will be described.

The grinding surface, which is the above grinding data, is aligned with the denture data with reference points to determine a grinding portion, thereby obtaining denture data reference points having grinding data. Here, based on the reference points, an important point is that a portion which should not be ground and a portion which should be ground are defined based on the reference points.

Therefore, by overlapping the indication parts of the reference points that represents a positional relationship between dentures and the reference point portions of the denture data with reference points having grinding data together, grinding portions of the dentures can be determined.

(7) A grinding step for pre-grinding dentures, which grinds a pre-grinding denture based on the denture data with reference points having grinding data, will be described. Grinding data is used as CAD data and create an NC program for processing in this step. This is a program of a computer numerical control (CNC) which controls a moving distance, a moving speed, and so on tools in machine work by a computer. Grinding of dentures is performed using this program.

2. Artificial Tooth Having Reference Point

Figure 7:
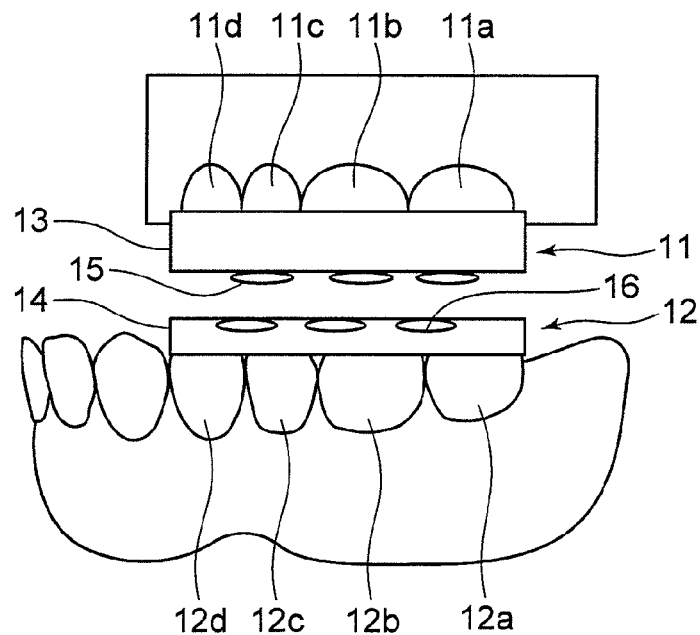
FIG. 7 is a side view illustrating coupling teeth on upper and lower jaws.

FIG. 7 illustrates artificial teeth having reference points, 11 and 12, according to the present invention.

Maxillary artificial teeth 11a, 11b, 11c, and 11d, which form a first molar tooth, a second molar tooth, a first premolar tooth, and a second premolar tooth, are connected to one another to constitute a maxillary (upper-jaw) coupling tooth 11. In the occlusal surface of each artificial tooth, a grinding section 13 is integrally formed and the cervical area thereof is approximately in the same form of the cervical area of a natural tooth.

Similarly, mandibular artificial teeth 12a, 12b, 12c, and 12d, which form a first molar tooth, a second molar tooth, a first premolar tooth, and a second premolar tooth, are connected to one another to constitute a mandibular coupling tooth 12. In the occlusal surface of each artificial tooth, a grinding section 14 is integrally formed and the cervical area thereof is approximately in the same form of the cervical area of a natural tooth.

The grinding section 13 of maxillary coupling tooth 11 has an area facing to the grinding section 14 of mandibular coupling tooth 12. In this area, three convexed portions 15 in the form of a spherical shape are formed. The convexed portions 15 form reference points of a maxillary artificial tooth.

Similarly, the grinding section 14 of maxillary coupling tooth 12 has an area facing to the grinding section 13 of mandibular coupling tooth 11. In this area, three concaved portions 16 in the form of a spherical shape are formed. The concaved portions 16 are fit to the convexed portions 15 of the grinding section 13 of the maxillary artificial tooth 11. The concaved portions 16 form reference points of a mandibular artificial tooth.

Figure 8:
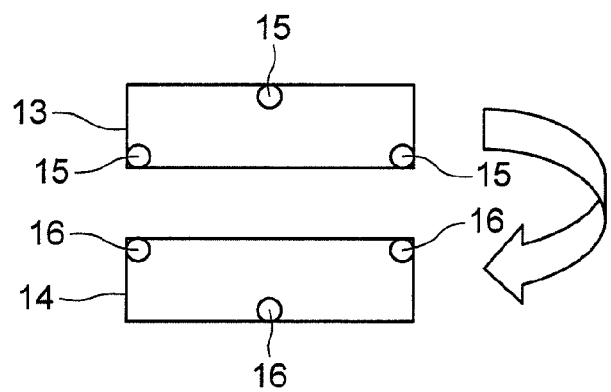
FIG. 8 is a plan view illustrating grinding sections of a coupling tooth.

As shown in FIG. 8, the grinding section 12 of maxillary coupling tooth 11 extends from the first molar to the second bicuspid. The convexed portions 15 of the grinding section 12 of maxillary coupling tooth 11 are formed at three portions: one on the center of the cheek side, one on the first molar side, and one on the second molar side. Similarly, the concaved portions 16 of the grinding section 14 of mandibular coupling tooth 12 are formed at three portions: one on the center of the cheek side, one on the first molar side, and one on the second molar side. However, the positions of convexed portions 15 and concaved portions 16 are not limited to the above positions and each of them may be located on any place.

The convexed portions 15 and concaved portions 16 are not restricted to those of spherical surfaces. Alternatively, the convexed portions may have a conic surface, that is, a needle-like shape and the concaved portions may be formed of a bowl shape. The positions of the convexed portions 15 and concaved portions 16 may be on the lateral sides of grinding sections 13 and 14.

A calculation method for obtaining a reference point from the convexed portion 15 and the concaved portion 16 is not specifically limited. However, it is preferable to obtain the spherical center of the spherical convexed or concaved portion 15 or 16 and give the resulting center as a reference point. The convexed portion 15 and the concaved portion 16 are designed to fit together, so that they can be used for maxillo-mandibular positioning.

Preferably, the positional relationship between reference points added to each of the molar teeth may be different from that of other molar teeth so that the type of the molar tooth or the corresponding position thereof can be identified from the positional relationship of the reference points on the molar tooth.

Figure 9:
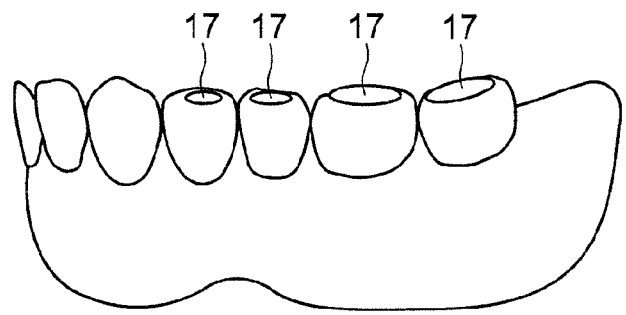
FIG. 9 is a side view illustrating artificial teeth having grinding sections in another form.
Figure 10:
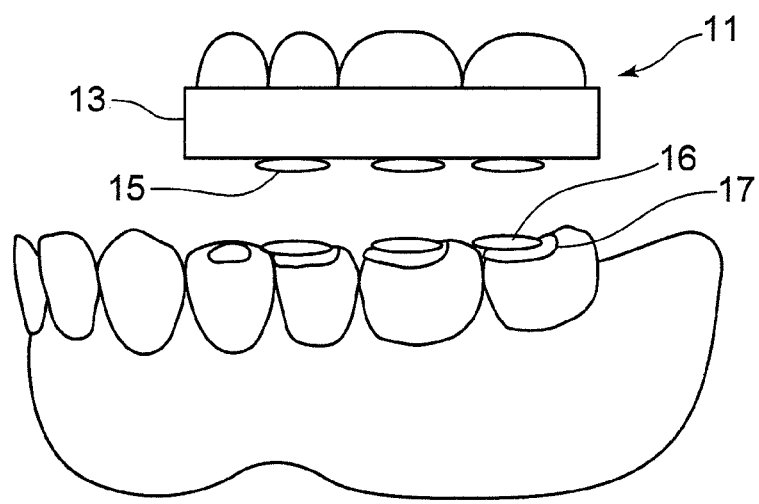
FIG. 10 is a side view illustrating a combination of a coupling tooth having grinding sections of FIG. 7 and a coupling tooth having grinding sections of FIG. 9.

As illustrated in FIG. 9, the grinding sections 17 are formed on the occlusal surfaces of the respective artificial tooth to reduce the amount of grinding. In this case, as illustrated in FIG. 10, the grinding section of the coupling tooth 11 on the opposite jaw may be formed as illustrated in FIG. 7 or may be formed on each of the occlusal surfaces of the respective artificial teeth just as in the case of the lower jaw. The material of the grinding section is the same enamel as an artificial tooth.

Each of the grinding sections 13, 14, and 17 is located in the occlusal surface direction from the maximum protruded portion of the artificial tooth, when being viewed from a direction perpendicular to the occlusal surface.

Figure 11:
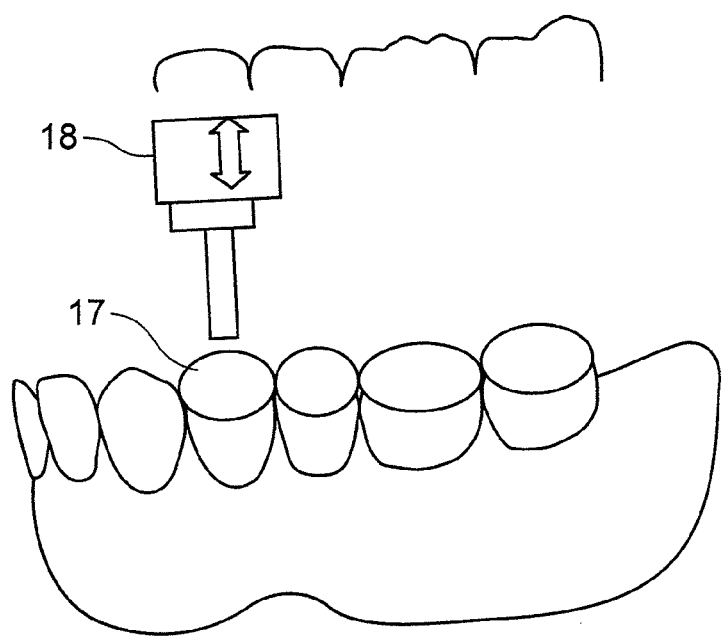
FIG. 11 is a diagram illustrating a situation of grinding the grinding section of a coupling tooth by an ultrasonic grinding machine.

The grinding sections 13, 14, and 17 are provided with their respective occlusal form data in advance. Thus, as illustrated in FIG. 11, grinding can be performed using a rotation cutting machine 18 according to the occlusal form data. A cutting tool having a pear-shaped tip is preferably used. When there is little grinding volume, an ultrasonic grinding machine with an ultrasonic vibrator may be used.

Occlusal form data shows a portion to be ground intentionally. For this reason, even if it is provided with neither a cusp nor a fossa, or a groove in advance, a cutting work can be performed in grinding. Data is held as "occlusal form data" for cutting. At the time of grinding, the above grinding method is employed to calculate and determine a grinding portion among those defined in "occlusal form data".

Next, the denture-manufacturing method using the artificial teeth having reference points will be described.

Figure 12:
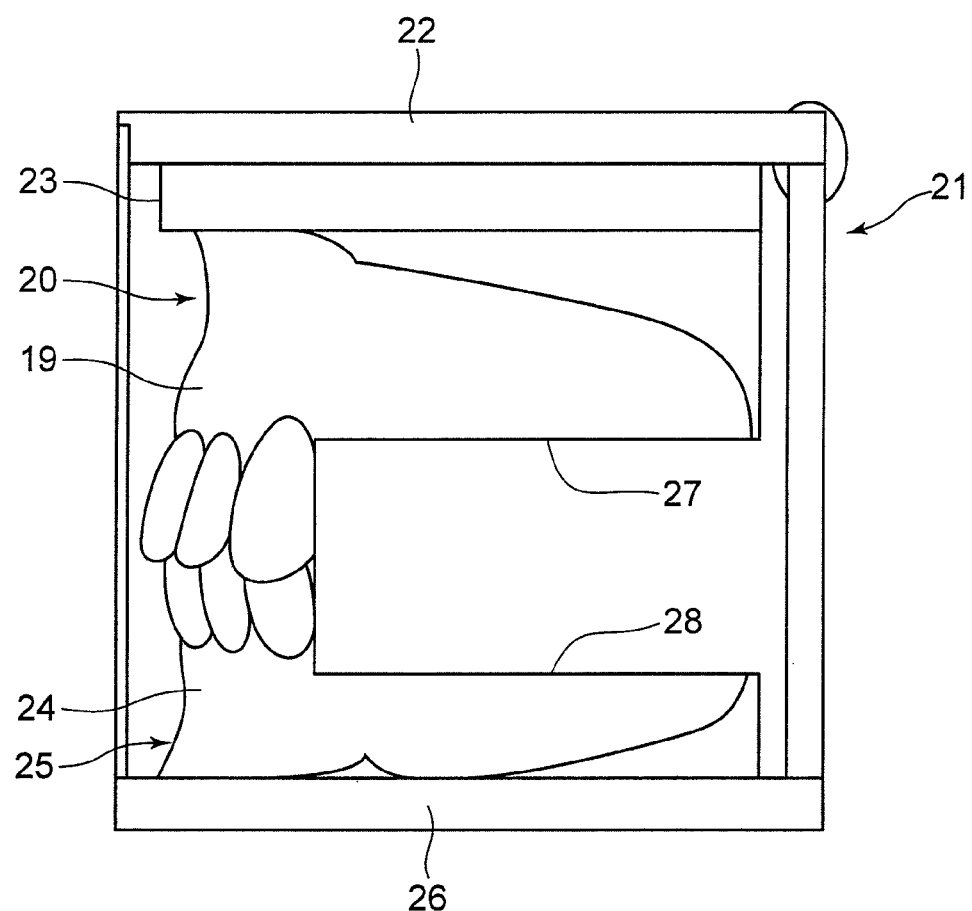
FIG. 12 is a side view illustrating a state of attaching an upper-jaw model and a lower-jaw model on an articulator.

As illustrated in FIG. 12, an upper-jaw model 20 of a patient with an attached wax rim. 19 is attached to an upper arch 22 of an articulator 21 through a spacer 23. Similarly, a lower-jaw model 25 of the patient with an attached wax rim 24 is attached to a lower arch 26 of the articulator 21. Reference points are previously formed on the upper arch 22 and the lower arch 26 of the articulator 21, respectively. A spacer 23 may be placed on the lower jaw or may be placed on both the upper and lower jaws. Notches 27 and 28 are formed in the respective portions where four molar teeth of the maxillomandibular wax rims 19 and 24 are arranged so that coupling teeth 11 and 12 of four molar teeth can be attached. As described in the grinding method, first, artificial teeth, which serve as anterior teeth, are arranged on the maxillomandibular wax rims 19 and 24, respectively.

Figure 13A:
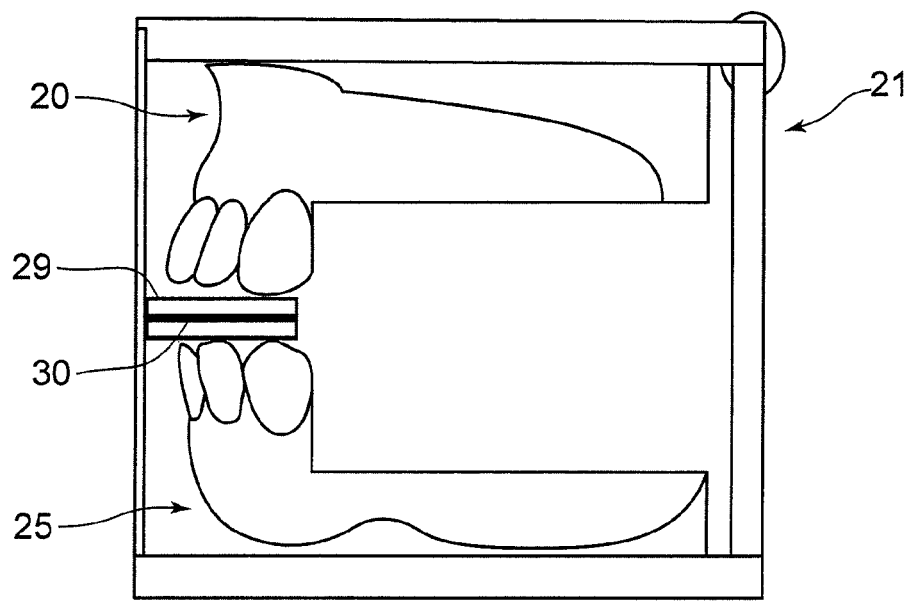
FIG. 13A and FIG. 13B are side views each illustrating a state where an arrangement auxiliary tool is placed between front teeth.
Figure 13B:
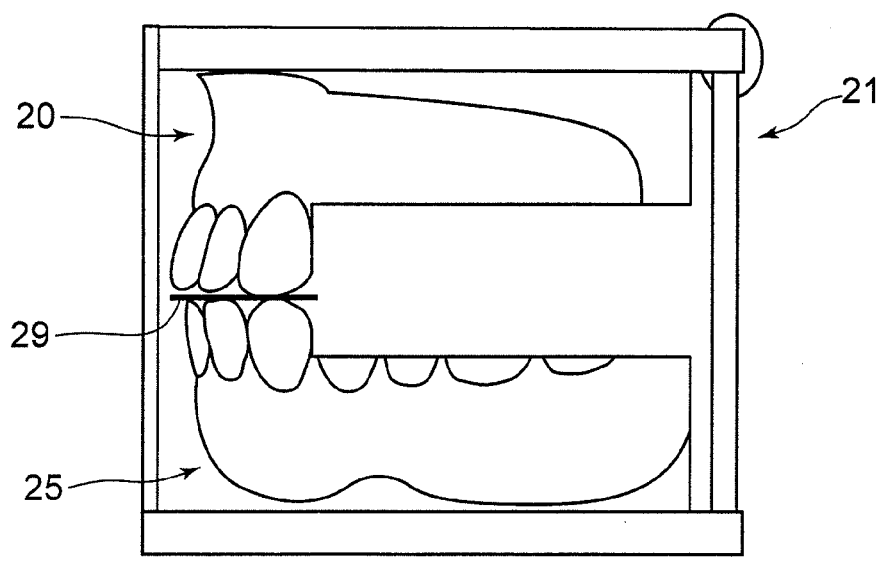

After arranging the artificial anterior teeth, the spacer 23 is removed. Then, as illustrated in FIG. 13, the upper-jaw model 20 is raised and an arrangement auxiliary tool 29 is placed between the upper-jaw front teeth and the lower-jaw front teeth.

The arrangement auxiliary tool 29 is a tabular-shaped material made of plastic or metal. The thickness of the arrangement auxiliary tool 29 may be determined in consideration of a gap formed between an upper-jaw front tooth and a lower-jaw front tooth when the spacer 23 is removed and the upper jaw is raised. When the spacer 23 is thick, as illustrated in FIG. 13A, a thick arrangement auxiliary tool 29 may be used. When the spacer 23 is thin, as illustrated in FIG. 13A, a thin arrangement auxiliary tool 29 may be used. In the case of the thick arrangement auxiliary tool 29, it is preferred to form an arrangement auxiliary line 30 extending in the centrifugal proximal direction from the front tooth to the molar tooth in the anterior extremity side of the arrangement auxiliary tool 29, as illustrated in FIG. 13A.

Figure 14:
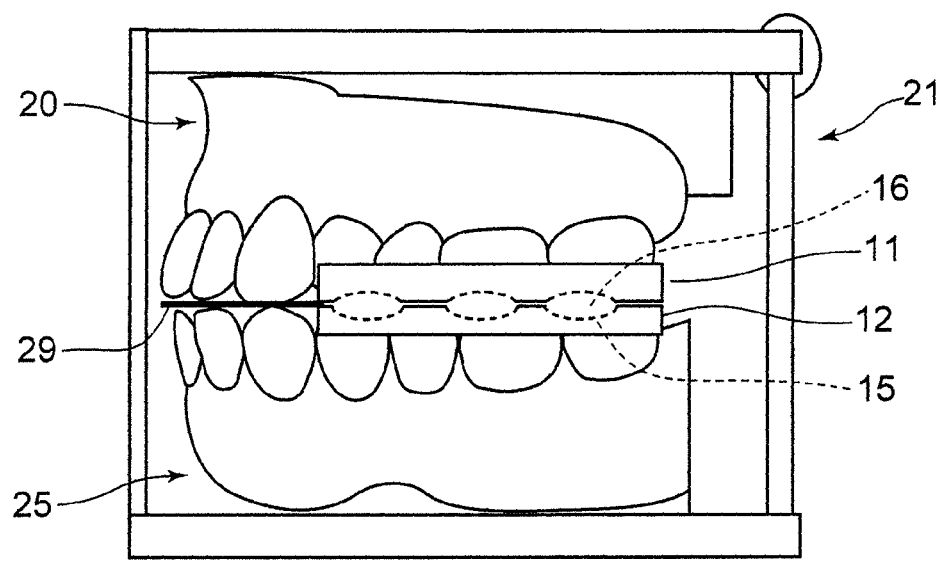
FIG. 14 is a side view illustrating a state where coupling teeth are arranged on an upper-jaw model and a lower-jaw model.

As shown in FIG. 14, in a state that the convexed portion 15 and the concaved portion 16 of each grinding section 13 and 17 are engaged with each other, the coupling tooth 11 of the upper jaw molar and the coupling tooth 12 of the lower jaw molar are mounted in the notches 27, 28 of the wax rim 19, 24 of the upper-jaw model 20 and the lower-jaw model 25. In this case, the heights of the coupling teeth 11, 12 are adjusted so that the joint of the grinding sections 13, 17 of the upper-jaw molar coupling tooth 11 and the lower-jaw molar coupling tooth 12 is in the same plane level as that of the arrangement auxiliary line 30 of the arrangement auxiliary tool 29.

Then, the upper-jaw model 20 and the lower-jaw model 25 are removed, just as in the cases of the above grinding method, the wax of residual ridges (wax rims) 19 and 24 are replaced with acrylic resin for denture plate by a lost wax process.

The reference points (artificial-tooth reference points) are read from the convexed portion 15 and the concaved portion 16 on maxillomandibular coupling teeth 11 and 12. The reference points (articulator reference points) of the articulator 21 used for arrangement of artificial teeth are also read. Then, occlusal surfaces are defined from these reference points with reference to the occlusal form data previously defined corresponding to the artificial-tooth reference points of the coupling teeth 11 and 12. A grinding portion is determined from each of these occlusal surfaces.

Figure 15A:
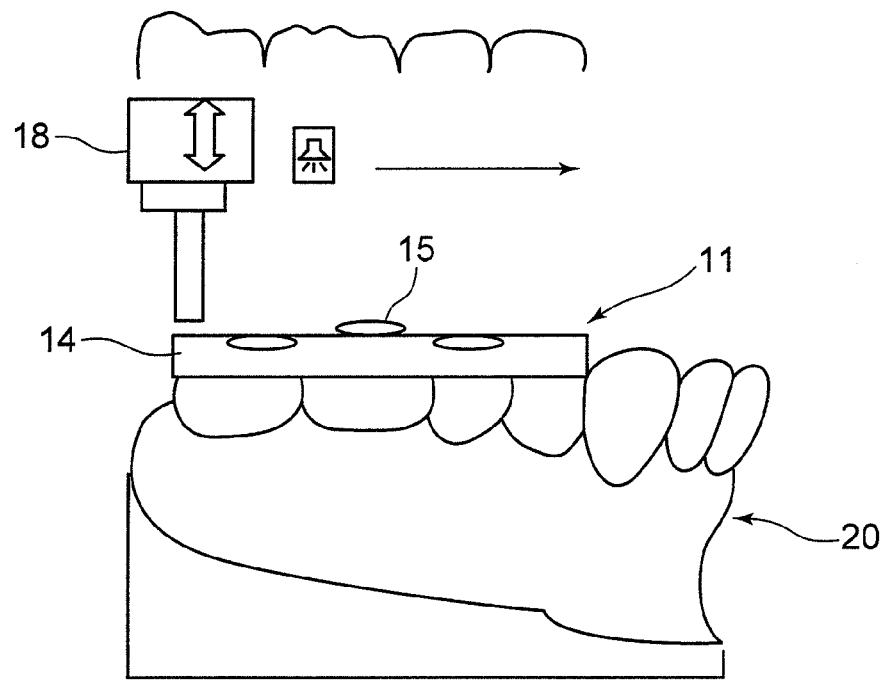
FIG. 15A and FIG. 15B are side views illustrating situations of grinding sections of coupling teeth on upper and lower jaws, respectively.
Figure 15B:
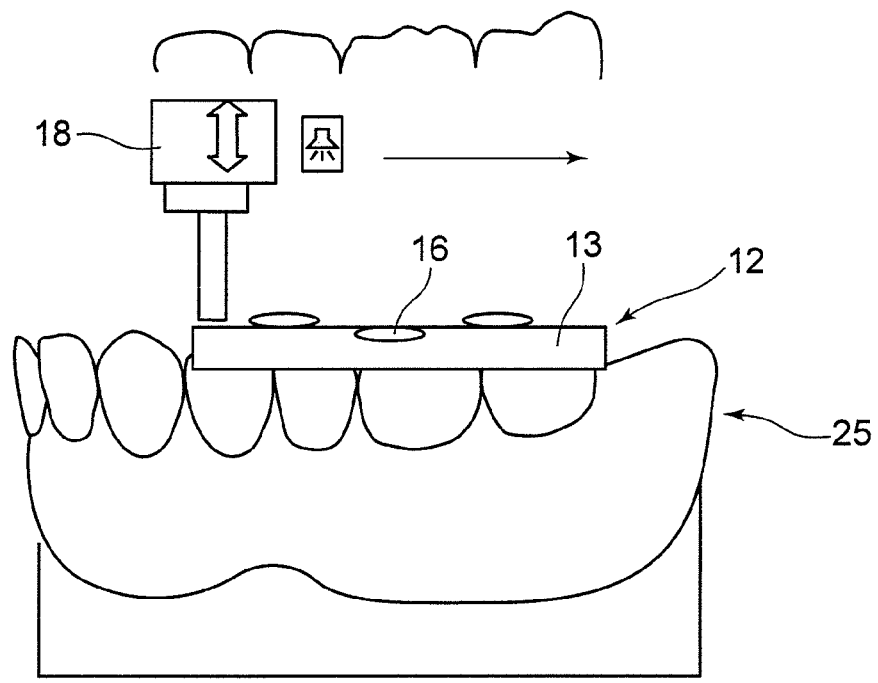

Next, as illustrated in FIG. 15, a rotation cutting machine 18 is used for grinding of the grinding sections 13 and 14 of the maxillary and mandibular coupling teeth 11 and 12 based on the grinding data of grinding sections 13 and 17. Thereby, the surfaces, convexed portions 15, and concaved portions 16 of grinding sections 13 and 14 are removed and occlusal surfaces including a cusp, a fossa, and groove is formed.

As a method for determining a grinding portion, in addition to the above method based on the occlusal form data previously provided for artificial teeth, there is a method that reproduces an occlusion stat in a three-dimensional space. This method is already described in the above grinding method. Thus the detailed description will be omitted. However, it will be described briefly below.

First, the three-dimensional reference point data are obtained. The three-dimensional reference point data includes the artificial-tooth reference points of the artificial tooth having reference point and the articulator reference points representing the position of the articulator on which the upper and lower jaws on which artificial teeth having reference point are arranged are attached. Next, from the acquired maxillomandibular three-dimensional reference point data, the positions of the maxillomandibular artificial teeth attached on the articulator are reproduced in a three dimensional space. Further, from the portion surrounded by a maxillomandibular image on the three-dimensional image of the reproduced occlusal state, the grinding data of grinding portion can be determined under dynamic conditions or set conditions. After grinding, removed portions of grooves and fossas may be determined.

What is claimed is:

1. A method for determining a grinding portion of pre-grinding dentures of maxillomandibular artificial teeth, the method comprising:

providing the pre-grinding dentures of maxillomandibular artificial teeth which have a grinding portion to be formed into an occlusal surface by grinding, and three or more reference points disposed on the grinding portion;

placing the pre-grinding dentures of maxillomandibular artificial teeth in a synthetic resin;

providing an articulator having an upper arch and a lower arch, each of the upper arch and the lower arch having three or more reference points;

reading the reference points of the pre-grinding dentures of maxillomandibular artificial teeth placed in the synthetic resin;

producing a three dimensional data of the pre-grinding dentures of maxillomandibular artificial teeth in a computer based on the read reference points of the pre-grinding dentures of maxillomandibular artificial teeth;

reading the reference points of the articulator;

producing a three dimensional data of the articulator in the computer based on the read reference points of the articulator;

calculating in the computer a position of the pre-grinding dentures of maxillomandibular artificial teeth mounted on the articulator so as to reproduce an occlusion state in the computer; and determining the grinding portion at a location where three dimensional data of the pre-grinding dentures of maxillomandibular artificial teeth overlap with each other.

2. A method for manufacturing a denture, the method comprising:

an anterior-teeth arrangement operation of attaching a patient's maxillomandibular model having a wax rim on an articulator with a spacer and arranging anterior teeth on the wax rim;

a preparation operation including removing the spacer;

an artificial teeth attaching operation of attaching artificial teeth on a molar portion of the wax rim on the maxillomandibular model, the artificial teeth having a grinding portion for being formed into an occlusal surface by grinding;

a lost wax operation of replacing the wax rim with an acrylic resin to obtain a denture plate by a lost wax process;

a grinding portion determination operation of reading an artificial-tooth reference point and an articulator reference point and determining a grinding portion from a previously determined occlusal surface of the artificial tooth corresponding to the artificial-tooth reference point, wherein the grinding portion determination operation includes determining a grinding portion of pre-grinding dentures of maxillomandibular artificial teeth by performing:

providing pre-grinding dentures of maxillomandibular artificial teeth which have a grinding portion to be formed into an occlusal surface by grinding, and three or more reference points disposed on the grinding portion;

placing the pre-grinding dentures of maxillomandibular artificial teeth in a synthetic resin;

providing an articulator having an upper arch and a lower arch, each of the upper arch and the lower arch having three or more reference points;

reading the reference points of the pre-grinding dentures of maxillomandibular artificial teeth placed in the synthetic resin;

producing a three dimensional data of the pre-grinding dentures of maxillomandibular artificial teeth in a computer based on the read reference points of the pre-grinding dentures of maxillomandibular artificial teeth;

reading the reference points of the articulator;

producing a three dimensional data of the articulator in the computer based on the read reference points of the articulator;

calculating in the computer a position of the pre-grinding dentures of maxillomandibular artificial teeth mounted on the articulator so as to reproduce an occlusion state in the computer; and determining the grinding portion at a location where three dimensional data of the pre-grinding dentures of maxillomandibular artificial teeth overlap with each other; and grinding the grinding portion.

3. The denture manufacturing method according to claim 2, wherein said preparation operation further includes placing an arrangement auxiliary tool between the maxillomandibular front teeth.

4. The denture manufacturing method according to claim 3, wherein the arrangement auxiliary tool is provided with an arrangement auxiliary line.

* * * * *